United States Patent [19]
Lewis et al.

[11] Patent Number: 6,012,577
[45] Date of Patent: Jan. 11, 2000

[54] MEDICAL DEVICE TRAY WITH LOCKABLE INNER LIDS

[75] Inventors: Paul P. Lewis; Greg S. Bell, both of Warsaw, Ind.

[73] Assignee: Paragon Medical, Inc., Pierceton, Ind.

[21] Appl. No.: 09/186,712

[22] Filed: Nov. 5, 1998

[51] Int. Cl.[7] ............................................. B65D 83/10
[52] U.S. Cl. ............................................. 206/370; 206/439
[58] Field of Search .................................. 206/438, 439, 206/363–366, 368, 369, 370, 561, 564; 220/523, 524, 254, 315, 334; 422/297, 300, 310

[56] References Cited

U.S. PATENT DOCUMENTS

| | | |
|---|---|---|
| 5,394,983 | 3/1995 | Latulippe et al. .................... 206/370 |
| 5,398,838 | 3/1995 | Dosunmu ............................... 220/524 |
| 5,628,970 | 5/1997 | Basile et al. .......................... 206/363 |
| 5,725,097 | 3/1998 | Bettenhausen et al. ............... 206/363 |
| 5,732,821 | 3/1998 | Stone et al. ........................... 206/370 |

Primary Examiner—B. Dayoan
Assistant Examiner—Luan K. Bui
Attorney, Agent, or Firm—Baker & Daniels

[57] ABSTRACT

A tray for housing medical devices such as instruments or implants. The tray includes a base having a plurality of pocket-like compartments to accommodate the devices. Individual inner lids are pivotally connected to the base and are each adapted to overlie a compartment in the base. The lids may be individually secured over the compartments or, alternatively, the top of the tray when secured over the base would overlie the lids so as to prevent their opening.

4 Claims, 4 Drawing Sheets

MEDICAL DEVICE TRAY WITH LOCKABLE INNER LIDS

SUMMARY OF THE INVENTION

This invention relates to a tray for holding medical devices, such as instruments and implants and will have specific but not limited application to a tray with its devices which may be sterilized.

The tray of this invention includes a plurality of pocket-like compartments into which the devices are placed in usually inventoried fashion. An inner lid, preferably one for each compartment, is provided. Each such lid is pivotally connected to the base of the tray and may be swung from a closed position overlying an individual compartment to an open position thereby exposing the devices within the compartment. When the top to the tray is applied over the base, it preferably adjacently overlies each inner lid, preventing the lid from being raised and thus serving to hold the devices in place within the underlying base compartment during movement of the tray. It is also preferable to provide a lock for each inner lid so that the lid may be secured in its closed position over its underlying compartment. In this manner the tray may be transported between different loaning or user entities with the reliance that if a particular inner lid has not been unlocked, that is its lock seal remaining unbroken, the contents of the underlying compartment remain as originally packaged and complete thus not requiring that a further inventory be taken.

Accordingly, it is an object of this invention to provide a tray for the storage of medical devices which has individual storage compartments with each compartment having a separate overlying lid.

Another object of this invention is to provide a medical device tray which includes a plurality of storage compartments each being separately securable.

Still another object of this invention is to provide a medical device tray which is of economical construction and within which individually compartmentalized devices, such as instrumentation may be retained in a secured state until usage.

Other objects of this invention will become apparent upon a reading of the following description.

BRIEF DESCRIPTION OF THE DRAWINGS

A preferred embodiment of this invention has been chosen for purposes of illustration and description wherein.

DESCRIPTION OF THE PREFERRED EMBODIMENT

Figure 1:
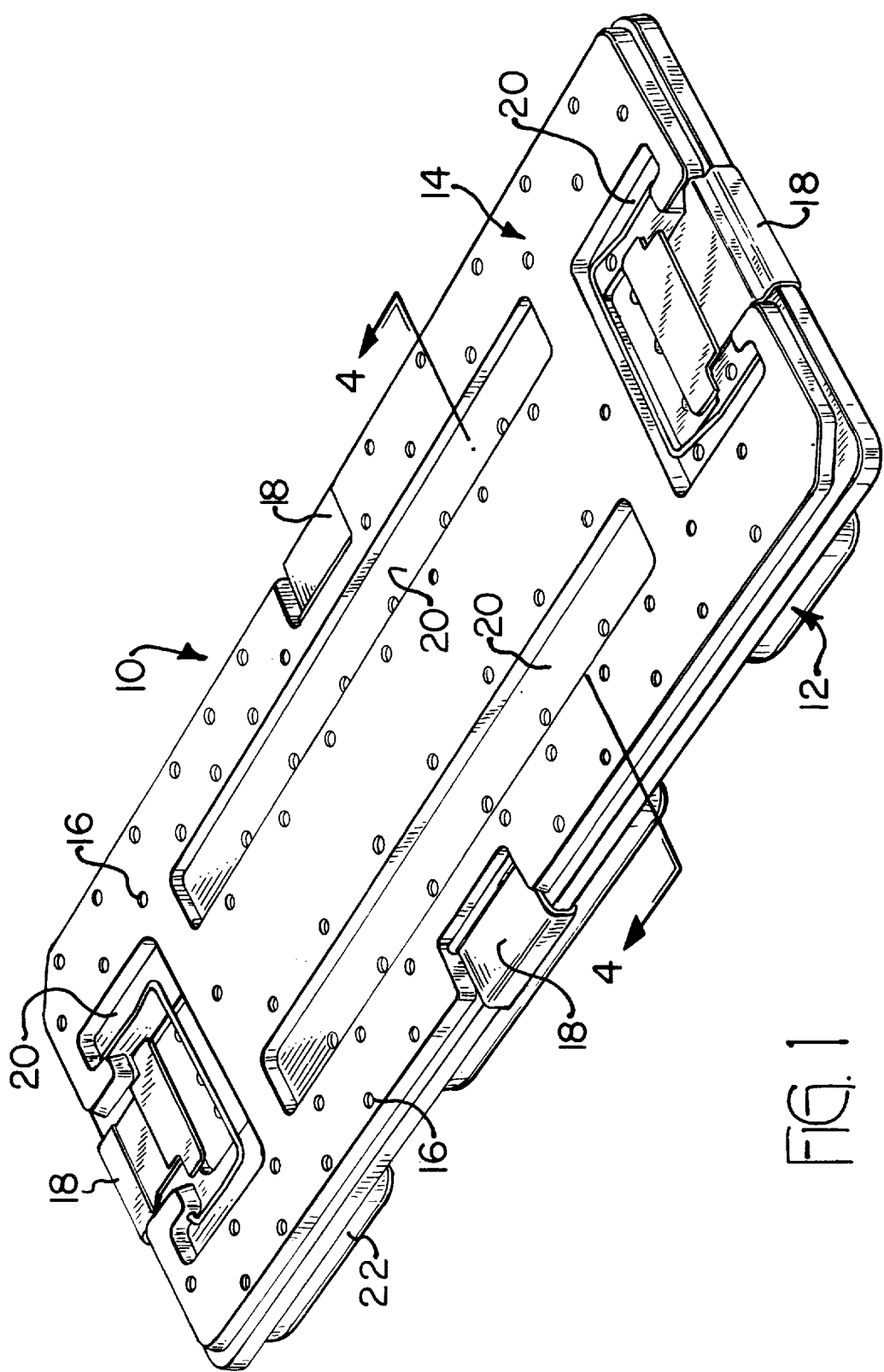
FIG. 1 is a perspective view of the tray with the top secured to the base of the tray.
Figure 4:
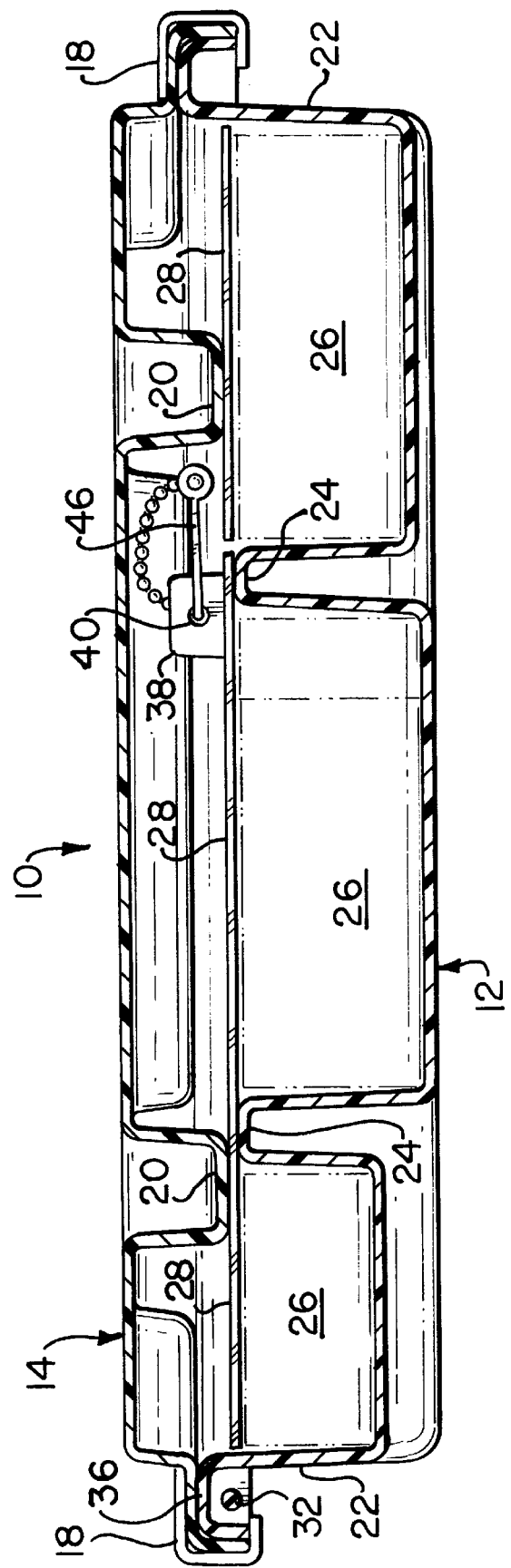
FIG. 4 is a cross-sectional view of the tray taken along line 4—4 of FIG. 1.

Case or tray 10 illustrated in the drawings includes a base 12 and a removable top 14. Both base 12 and top 14 of tray 10 include a plurality of openings 16 through which sterilization steam may pass during instrument or implant sterilization. Top 14 is secured over base 12 as illustrated in FIGS. 1 and 4 by latches 18 which are of common construction and operation in the industry.

Top 14 is provided with a plurality of selectively spaced recessed wall parts 20 whose purpose and function will be later explained. Base 12 of tray 10 includes a side wall 22 and an upper wall 24. Formed in upper wall 24 of base 12 are a plurality of selectively positioned pocket-like compartments 26 which serve as depositories for the medical devices which are not shown. Selected compartments 26 may be provided with protruding ribs into which the devices are located when stored within the compartment. Other compartments may house flexible holders to support the devices within the compartments.

Figure 2:
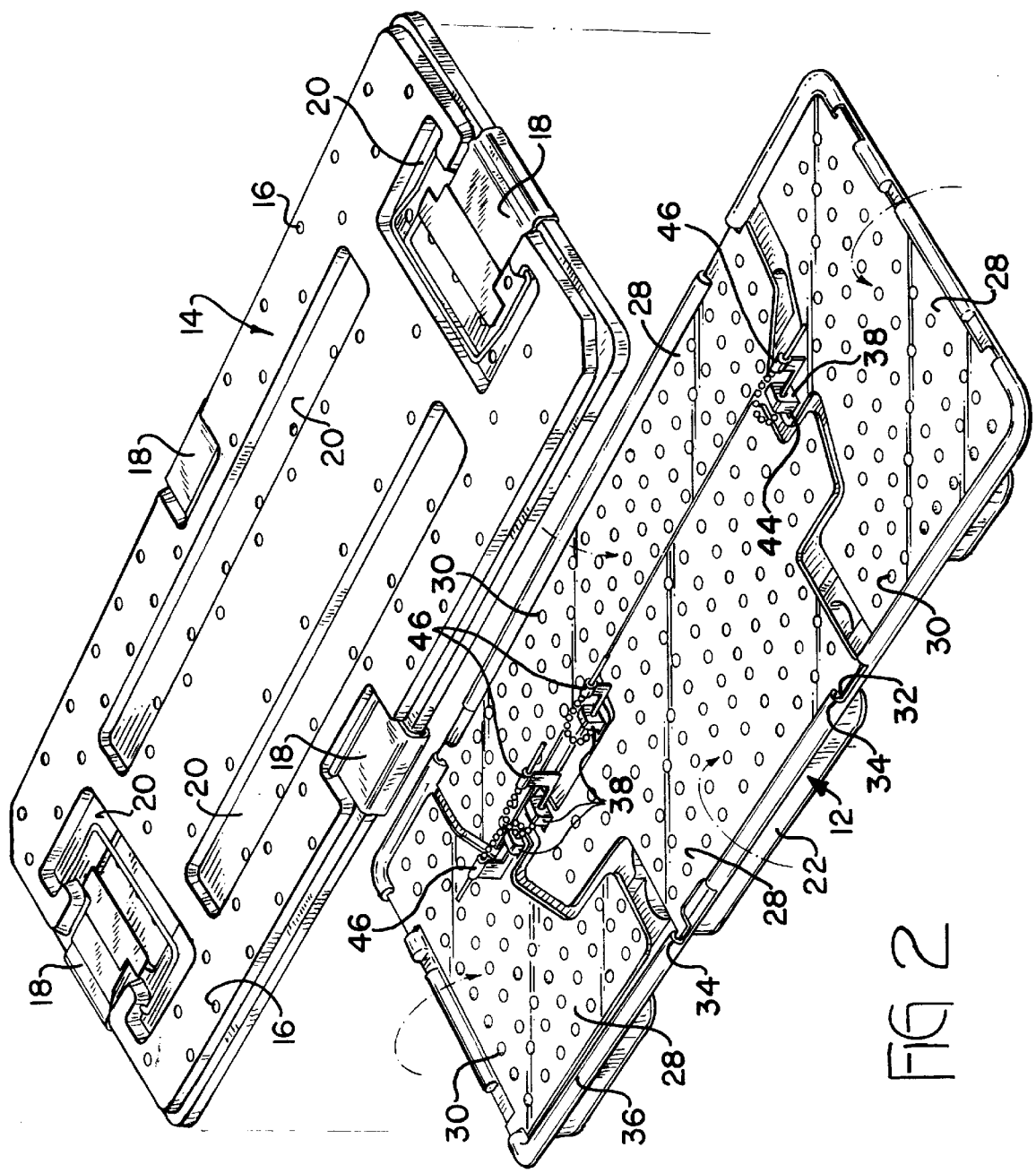
FIG. 2 is a perspective view of the tray showing the top in an open or raised position to expose the interior of the base with its inner lids in their closed positions.
Figure 3:
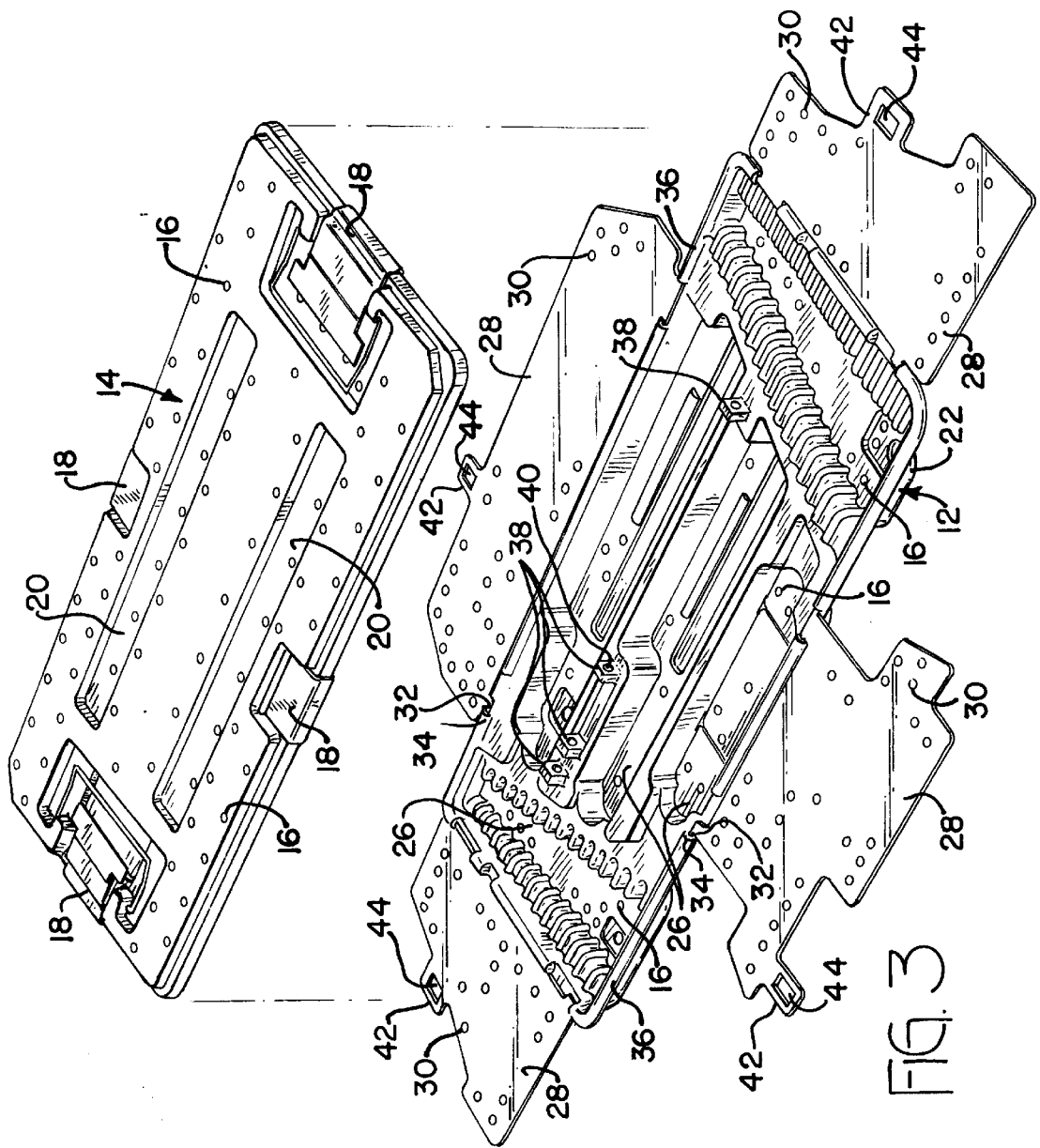
FIG. 3 is a perspective view of the tray with the top raised and with the individual inner lids unlocked and shifted into their open positions to expose the interior of the base and the individual compartments.

Attached to base 12 for pivotal movement are one or more inner lids 28. Preferably, there is a separate inner lid 28 for each compartment 26. Inner lids 28 are preferably planar in form, having a plurality of openings 30 through which the sterilization steam may pass during the sterilization process. Each lid 28 is secured next to its adjacently underlying compartment 26 by being provided with a pair of peripheral pintles 32 each rotatably fitted into a gudgeon 34 formed in the upper margin 36 of base 12. In this manner each inner lid 28 may be pivoted from the closed position overlying its associated compartment 26 as seen in FIG. 2 to the open position shown in FIG. 3 to expose the compartment and its devices.

Upper wall 24 of base 12 is formed with upwardly extending lug-like protrusions 38 each having an opening 40 through it. Correspondingly, each inner lid 28 includes a laterally projecting tab part 42 into which a large opening 44 is formed. Each lid tab part 42 with its opening 44 is positioned so that when the lid is swung into its closed position such as shown in FIG. 2, the lid rests upon upper wall 24 with a protrusion 38 projecting upwardly through the lid's tab part opening 44. To individually secure each inner lid 28 over its underlying compartment 26, a lock pin 46 is inserted through opening 40 in each protrusion 38 so as to overlie the tab part 42 and thus retain the lid 28 in its closed position over the underlying compartment 26. Each lock pin 46 is preferably of the sealed type so that to remove the pin its seal must be broken. In this manner, each compartment 26 with its inner lid 28 may be segregated from the remainder of the base 12 with any enclosed devices within the compartment being securely retained until the lock pin seal is broken and the pin removed so as to allow the lid to be shifted from its closed and locked position shown in FIG. 2 to the open position shown in FIG. 3, thereby exposing the devices for usage.

In FIG. 4, top 14 of tray 10 is shown in its closed position over base 12 with its recessed wall parts 20 either contacting or being spaced slightly above the underlying closed inner lids 28 so as to retain the lids in their closed positions resting upon top wall 24 of base 12. In this manner each lid 28 completely encloses the underlying compartment irrespective of the existence and placement of the lock pins 46. Thus, the devices in each individual compartment enclosed by an overlying lid 28 remain segregated from the remainder of the devices in the tray while the top 14 covers base 12 even in the absence of the use of any lock pins 46. When lock pins 46 are utilized to secure lids 28, there is a visual indicator which tells the user of the tray that the devices within the locked and sealed compartment has not been removed or utilized.

This invention is not limited to the details above given but may be modified within the scope of the appended claims.

What we claim is:

1. A medical device tray comprising a base and a removable top for spanning said base, said base including a side wall and an upper wall interrupted by a plurality of recessed compartments, said compartments serving as means for receiving medical devices, a plurality of lids, each of said lids pivotally connected to said base and being shiftable between a closed position overlying a said compartment and an open position exposing the interior of said last-mentioned compartment, each lid being securable against said shiftable movement when in its said closed position, said top overlying each lid in its closed position when spanning said base.

2. The tray of claim 1 and a removable lock device associated with each lid, each lock device engaging its associated lid and said base to secure said associated lid in its said closed position overlying a said compartment.

3. The tray of claim 1 wherein each lid rests against said base upper wall when the lid is in its said closed position, said top adjacently overlying each lid when in its said closed position with the top spanning said base.

4. The tray of claim wherein said top contacts each lid when in its said closed position with the top spanning said base.

* * * * *

UNITED STATES PATENT AND TRADEMARK OFFICE
CERTIFICATE OF CORRECTION

PATENT NO. : 6,012,577

DATED : January 11, 2000

INVENTOR(S) : Paul P. Lewis and Greg S. Bell

It is certified that error appears in the above-identified patent and that said Letters Patent are hereby corrected as shown below:

Claim 4, Line 1 - Insert the number "3" after the word claim.

Signed and Sealed this

First Day of August, 2000

Attest:

Q. TODD DICKINSON

Attesting Officer

Director of Patents and Trademarks